United States Patent [19]
Kubo et al.

[11] Patent Number: 5,639,773
[45] Date of Patent: Jun. 17, 1997

[54] OCULAR HYPOTENSIVE AGENT

[75] Inventors: Keiji Kubo, Minoo; Takahiro Ogawa, Nishinomiya; Takaaki Deguchi, Kobe, all of Japan

[73] Assignees: Senju Pharmaceutical Co., Ltd.; Takeda Chemical Industries, Ltd., both of Osaka, Japan

[21] Appl. No.: 269,675

[22] Filed: Jul. 1, 1994

[30] Foreign Application Priority Data

Jul. 2, 1993 [JP] Japan ................................. 5-164847

[51] Int. Cl.$^6$ ........................ A61K 31/41; A61K 31/415
[52] U.S. Cl. ........................ 514/382; 514/395; 514/510; 514/559; 514/560; 514/569; 514/577
[58] Field of Search ........................ 514/382, 395, 514/510, 559, 560, 569, 577; 548/250, 306.1, 306.4, 314.7, 325.5, 354.1, 355.1

[56] References Cited

U.S. PATENT DOCUMENTS

| | | | |
|---|---|---|---|
| 5,102,903 | 4/1992 | Smith | 514/406 |
| 5,128,356 | 7/1992 | Naka et al. | 514/381 |
| 5,162,326 | 11/1992 | Naka et al. | 514/269 |
| 5,183,899 | 2/1993 | Naka et al. | 548/253 |
| 5,250,554 | 10/1993 | Naka et al. | 514/381 |
| 5,284,661 | 2/1994 | Morimoto et al. | 424/464 |

FOREIGN PATENT DOCUMENTS

| | | | |
|---|---|---|---|
| 0400835 | 12/1990 | European Pat. Off. | |
| 0 400 835 | 12/1990 | European Pat. Off. | C07D 235/08 |
| 0459136 | 4/1991 | European Pat. Off. | C07D 235/26 |
| 0 430 300 | 6/1991 | European Pat. Off. | C07D 473/00 |
| 0 434 038 | 6/1991 | European Pat. Off. | C07D 471/04 |
| 0 445 811 | 9/1991 | European Pat. Off. | C07D 213/80 |
| 0 588 299 | 3/1992 | European Pat. Off. | C07D 413/12 |
| 0 483 683 | 5/1992 | European Pat. Off. | C07D 495/04 |
| 0 518 033 | 12/1992 | European Pat. Off. | C07D 471/04 |
| 0 520 423 | 12/1992 | European Pat. Off. | C07D 413/10 |
| 0 603 712 | 6/1994 | European Pat. Off. | C07D 413/10 |
| 91/15206 | 10/1991 | WIPO | A61K 31/41 |
| 91/16313 | 10/1991 | WIPO | C07D 235/04 |

OTHER PUBLICATIONS

FASB J.S., A1218 (1991), S. Wilson et al., "The Ocular Hypotensive Effect of DUP 753, a Non-Peptide Agiotensin II Antagonist", p. 4918.

Curr. Eye Res., 8, 841–849 (1989), Mallorga et al., "Angiotensin II Receptors Labelled with $^{125}$I-[Sar$^1$, Ile$^8$] AII in Abino Rabbit Ocular Tissues", pp. 841–849.

J. Ocular Pharmacol., 3, 295–307 (1988), Watkins et al.

Am. J. Ophthalmol., 105, 674–677 (1988), Constad et al.

Constad et al., "Use of an AngiotensinConverting Enzyme Inhibitor in Ocular Hypertension and Primary Open–Angle Glaucoma", *American Journal of Ophthalmology*, vol. 105:674–677, (1988).

Journal of Pharmacol. Exp. Ther., vol. 266(3), Kawamura et al., "TCV 116, a Novel Angiotensin II Receptor Antagonist . . . Carotid Injury in Rats", 1993, abstract.

*Primary Examiner*—C. Warren Ivy
*Assistant Examiner*—Rosalynd Williams
*Attorney, Agent, or Firm*—Foley & Lardner

[57] ABSTRACT

This invention relates to an ocular hypotensive agent which comprises a compound represented by the formula:

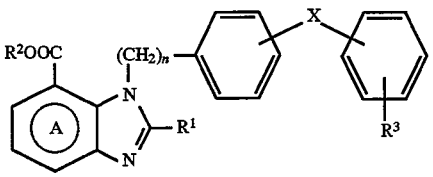

wherein $R^1$ represents hydrogen or an optionally substituted hydrocarbon residue that may be bound via a hetero atom; $R^2$ represents hydrogen or a hydrocarbon residue that may have a substituent; $R^3$ represents a group capable of forming an anion or a group capable of changing thereto; X is a covalent bond between the 2 benzene rings or a spacer having a chain length of 1 to 2 atoms as the linear moiety between the adjoining phenylene group and phenyl group; n represents 1 or 2; ring A is a benzene ring having 1 or 2 optional substituents in addition to the group represented by COOR$^2$, or a pharmaceutically acceptable salt thereof.

10 Claims, No Drawings

OCULAR HYPOTENSIVE AGENT

FIELD OF THE INVENTION

This invention relates to an ocular hypotensive agent.

BACKGROUND OF THE INVENTION

Glaucoma, a pathologic state in which intraocular pressure exceeding the normal range of 10–20 mmHg results in eyesight disorder, is among the intractable ophthalmopathies. Recently, the incidence of low tension glaucoma has increased. Low tension glaucoma, occurs when intraocular pressure is less than 21 mmHg, which reduces the field of vision and impairs ocular blood flow. The current therapy for glaucoma, including low tension glaucoma is to lower intraocular pressure. For glaucoma chemotherapy, choline agonists, represented by pilocarpine, and anti-choline esterase agents have long been used as eyedrops. These drugs, however, cause severe side effects such as iridic cystoma, iris synechia, cataract and retinal detachment when used in long-term continuous administration, as well as a sensation of darkness due to mydriasis, eye injection and other symptoms.

Although sympathetic nerve agonists such as epinephrine and dipivefrine have been used for their ocular hypotensive action, their use is limited to open-angle glaucoma, and can cause mydriasis, blepharitis and conjunctival pigmentation and systemic symptoms such as increased heart rate and hypertension.

In recent years, β-blockers such as timolol, pindolol and carteolol have been widely used, since they are advantageous in that their instillation suppresses aqueous humor production to lower ocular tension, without acting on the pupil. These drugs, however, tend to cause local symptoms such as feelings of eye dryness, allergic blepharitis and superficial keratitis.

The only group of ocular hypotensive agents that can be used systemically in long-term continuous administration is carbonic acid dehydrogenase inhibitors such as acetazolamide and metazolamide, but these can cause gastrointestinal disorder, ureteroliths and electrolytic anomalies.

In recent years, angiotensin-converting enzyme inhibitors (e.g., Japanese Published unexamined patent application (Kokai tokkyo koho) Nos. 21614/1984, 130816/1984, 209527/1985, 10553/1986, 203665/1988 and 218612/1990), which inhibit the renin-angiotensin system involved in blood pressure regulation, have been reported as useful glaucoma remedies [J. Ocular Pharmacol., 3, 295–307 (1987); Am. J. Ophthalmol., 105, 674–677 (1988)], but none have seen practical application.

Compounds exhibiting angiotensin II antagonistic action are known to serve as therapeutic agents for circulatory diseases such as hypertension, heart diseases (heart hypertrophy, heart failure, myocardial infarction etc.), cerebral stroke and nephritis. Concerning their mechanism of action, inhibition of binding to angiotensin II receptors, a potent vasoconstrictor, has been suggested. Japanese Published unexamined application (kokai tokkyo koho) Nos. 63264/1991, 27362/1991 and 184976/1991 state that angiotensin II antagonists can be used to treat glaucoma.

As stated above, there is not a satisfactory drug offering efficient ocular tension reduction with low side effects.

OBJECT OF THE INVENTION

This invention provides an ocular hypotensive agent possessing excellent activity for lowering intraocular pressure.

SUMMARY OF THE INVENTION

Against this background and focusing on ciliary epithelial angiotensin II receptors, the present inventors, in the search for an agent for lowering intraocular pressure more efficiently with low side effects, investigated compounds that act on the angiotensin system to alter ciliary vascular motion and effectively cause an activity for lowering intraocular pressure without side effects, and as a result developed the present invention.

Accordingly, the present invention relates to (1) an ocular hypotensive agent which comprises a compound represented by formula (I):

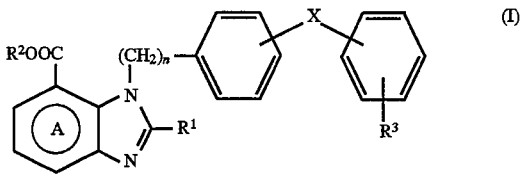

wherein $R^1$ represents hydrogen or an optionally substituted hydrocarbon residue that may be bound via a hetero atom; $R^2$ represents hydrogen or a hydrocarbon residue that may have a substituent; $R^3$ represents a group capable of forming an union or a group capable of changing thereto; X is a covalent bond between the two benzene rings or a spacer having a chain length of 1 to 2 atoms as the linear moiety between the adjoining phenylene group and phenyl group; n represents 1 or 2; ring A is a benzene ring having 1 or 2 optional substituents in addition to the group represented by COOR², or a pharmaceutically acceptable salt thereof, (2) the agent of the above mentioned (1), wherein the formula (I) is represented by formula:

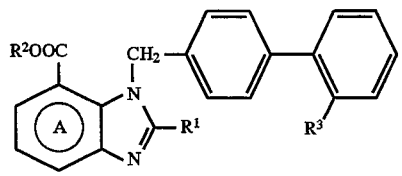

wherein $R^1$ represents hydrogen or a lower ($C_{1-6}$) alkoxy; $R^2$ represents hydrogen or a lower ($C_{1-4}$) alkyl that may be substituted with hydroxy, amino, halogen, a lower ($C_{2-6}$) alkanoyloxy, a lower ($C_{4-7}$) cycloalkanoyloxy, a lower ($C_{1-6}$) alkoxycarbonyloxy, a lower ($C_{3-7}$) cycloalkoxycarbonyloxy or a lower ($C_{1-4}$) alkoxy; $R^3$ stands for tetrazolyl, carboxyl or a group represented by the formula:

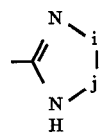

wherein i stands for —O— or —S—; j stands for >C=O, >C=S or >S(O)$_m$; and m is 0, 1 or 2; ring A stands for a benzene ring which may have one or two substituents in addition to COOR².

(3) the agent of the above mentioned (1), which is for local administration to the eye, (4) the agent of the above mentioned (3), which is eyedrops or ophthalmic ointment, (5) the agent of the above mentioned (4), wherein a concentration of the compound represented by the above mentioned formula (I) or salt thereof is 0.001 to 10 w/v % or w/w %, (6) an agent for the prophylaxis or treatment of glaucoma which comprises the compound represented by the above mentioned formula (I) or pharmaceutically acceptable salt thereof, (7) an agent for the prophylaxis or treatment of diseases caused by a rise of ocular pressure which comprises the compound represented by the above mentioned formula (I) or pharmaceutically acceptable salt thereof, and (8) the agent of the above mentioned (7), wherein the diseases include glaucoma.

DETAILED DESCRIPTION OF THE INVENTION

The most significant structural feature of the compound used in the ocular hypotensive agent of the present invention, represented by general formula (I) above, is the presence of both $COOR^2$ and $R^3$. Such a structure ensures excellent action for lowering intraocular pressure.

Not every angiotensin II receptor antagonizing compound is effective in the treatment of glaucoma, since a sufficient amount of drug to lower ocular tension must pass the blood aqueous humor barrier in the case of oral administration, the drug being unable to antagonize the angiotensin II receptor on the corpus ciliare unless it first passes the corneum, in the case of local administration to the eye. Another reason is that the desired efficacy cannot be obtained even when the drug has reached the receptor site, unless it remains there in sufficient concentration for a sufficient period of time to lower ocular tension. Also, special attention is required in choosing a drug for local administration to the eye because the drug's ocular irritativity, if any, can aggravate symptoms. As well, when the drug is administered in a dosage form of aqueous ophthalmic solution, it is preferable that the drug be stable in aqueous solutions without active ingredient decomposition or insoluble foreign matter formation.

Possessing angiotensin II receptor antagonizing action, the compound of the present invention, represented by formula (I), can be advantageously used as an ocular hypotensive agent.

Examples of the hydrocarbon residue represented by $R^1$ include alkyl, alkenyl, alkynyl, cycloalkyl, aryl and aralkyl groups. Among them alkyl, alkenyl and cycloalkyl groups are preferable. The hydrocarbon residue may bind to the benzimidazole ring through a hetero atom.

The alkyl group represented by $R^1$ is a straight-chain or branched lower alkyl group having 1 to about 8 carbon atoms, as exemplified by methyl, ethyl, propyl, isopropyl, butyl, isobutyl, sec-butyl, t-butyl, pentyl, i-pentyl, hexyl, heptyl or octyl.

The alkenyl group represented by $R^1$ is a straight-chain or branched lower alkenyl group having 2 to about 8 carbon atoms, as exemplified by vinyl, propenyl, 2-butenyl, 3-butenyl, isobutenyl or 2-octenyl.

The alkynyl group represented by $R^1$ is a straight-chain or branched lower alkynyl group having 2 to about 8 carbon atoms, as exemplified by ethynyl, 2-propinyl, 2-butynyl, 2-pentynyl or 2-octynyl.

The cycloalkyl group represented by $R^1$ is a lower cycloalkyl group having 3 to about 6 carbon atoms, as exemplified by cyclopropyl, cyclobutyl, cyclopentyl or cyclohexyl.

The above-mentioned alkyl, alkenyl, alkynyl or cycloalkyl group may optionally be substituted with hydroxyl group, an optionally substituted amino group (e.g. amino, N-lower ($C_{1-4}$) alkylamino or N,N-dilower ($C_{1-4}$) alkylamino), halogen, a lower ($C_{1-4}$) alkoxy group, a lower ($C^{1-4}$) alkylthio group.

The aralkyl group represented by $R^1$ is, for example, a phenyl-lower ($C_{1-4}$) alkyl such as benzyl or phenethyl, and the aryl group represented by $R^1$ is, for example, phenyl.

The above-mentioned aralkyl or aryl group may optionally have, on any position of its benzene ring, for example, halogen (e.g. F, Cl or Br), nitro, an optionally substituted amino group (e.g. amino, N-lower ($C_{1-4}$) alkylamino or N,N-dilower ($C_{1-4}$) alkylamino), lower ($C_{1-4}$) alkoxy (e.g. methoxy or ethoxy), lower ($C_{1-4}$) alkylthio (e.g. methylthio or ethylthio) or lower ($C_{1-4}$) alkyl (e.g. methyl or ethyl).

Among the above-mentioned groups represented by $R^1$, optionally substituted alkyl, alkenyl or cycloalkyl groups (e.g. a lower ($C_{1-5}$) alkyl, lower ($C_{2-5}$) alkenyl or lower ($C_{3-6}$) cycloalkyl group optionally substituted with hydroxyl group, amino group, halogen or a lower ($C_{1-4}$) alkoxy group) are preferable.

The above-mentioned $R^1$ may optionally bind through a hetero-atom (e.g. nitrogen ($N(R^4)$ ($R^4$ stands for hydrogen or a lower ($C_{1-4}$) alkyl)), oxygen or sulfur ($-S(O)_m-$ (m denotes an integer of 0 to 9.)), etc.), and, among them, alkyl or alkenyl group bound through a hetero-atom (e.g. methylamino, ethylamino, propylamino, propenylamino, isopropylamino, allylamino, butylamino, isobutylamino, dimethylamino, methylethylamino, methoxy, ethoxy, propoxy, isopropoxy, propenyloxy, allyloxy, butoxy, isobutoxy, sec-butoxy, t-butoxy, 2-butenyloxy, 3-butenyloxy, isobutenyloxy, pentoxy, isopentoxy, hexyloxy, methylthio, ethylthio, propylthio, isopropylthio, allylthio, butylthio, isobutylthio, sec-butylthio, t-butylthio, 2-butenylthio, 3-butenylthio, isobutenylthio, pentylthio, isopentylthio, hexylthio, etc.) are preferable, with greater preferance given to a lower $C_{1-4}$ alkoxy (e.g. methoxy, ethoxy, propoxy, isopropoxy, butoxy, isobutoxy, sec-butoxy, t-butoxy).

With respect to formula (I) above, the group for $R^3$, capable of forming an anion (a group having a hydrogen atom capable of leaving as a proton), or a group capable of changing thereto, is exemplified by 5- to 7- membered (preferably 5- or 6- membered) monocyclic heterocyclic ring residues which contain one or more of N, S and O and which may be substituted (preferably N-containing heterocyclic residues having a hydrogen atom capable of leaving as a proton), and groups capable of changing thereto in vivo. Such groups include the following:

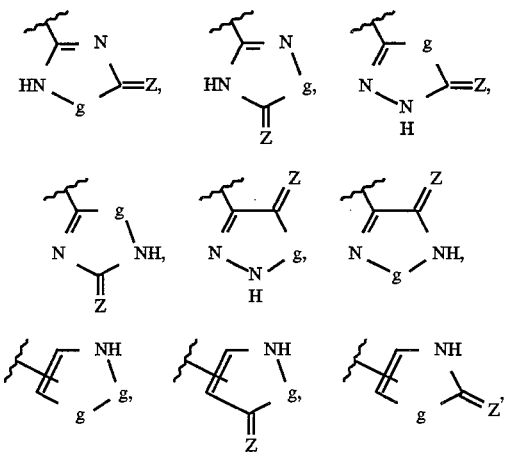

-continued

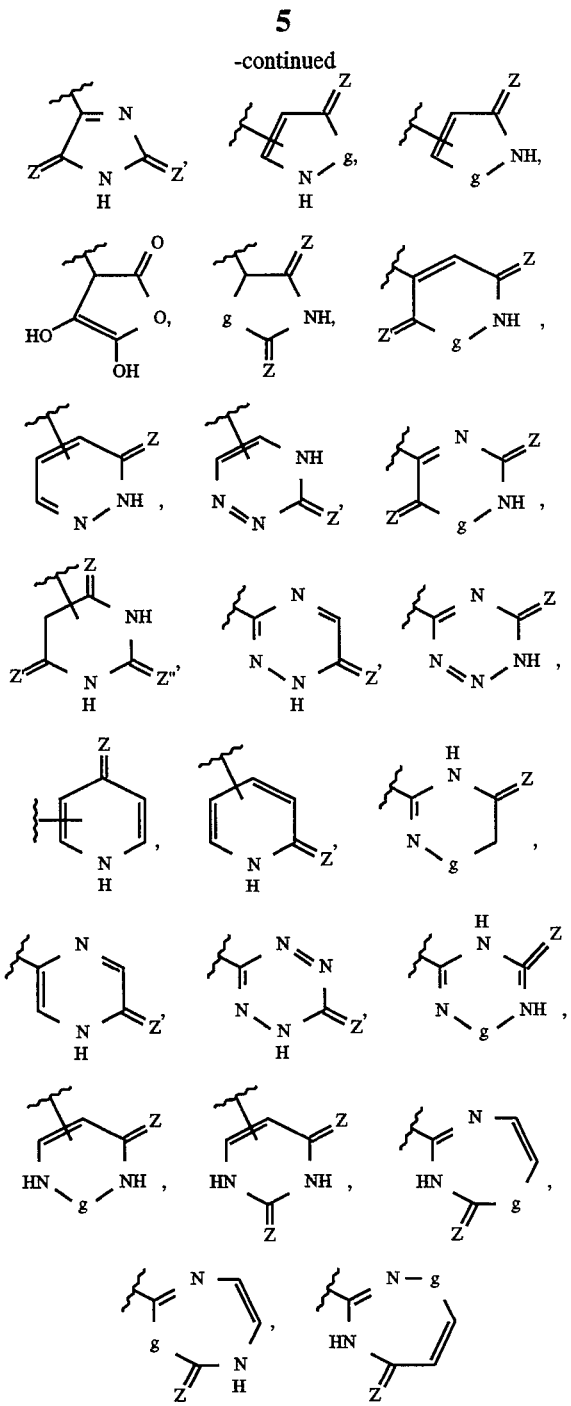

The chemical bond between the group for R³ and the partner phenyl group may be a carbon-carbon bond as shown above, or a nitrogen-carbon bond via one of the several nitrogen atoms when the symbol g stands for —NH— in the above formulas. For instance, when R³ is represented by

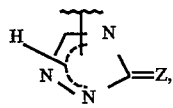

embodiments are

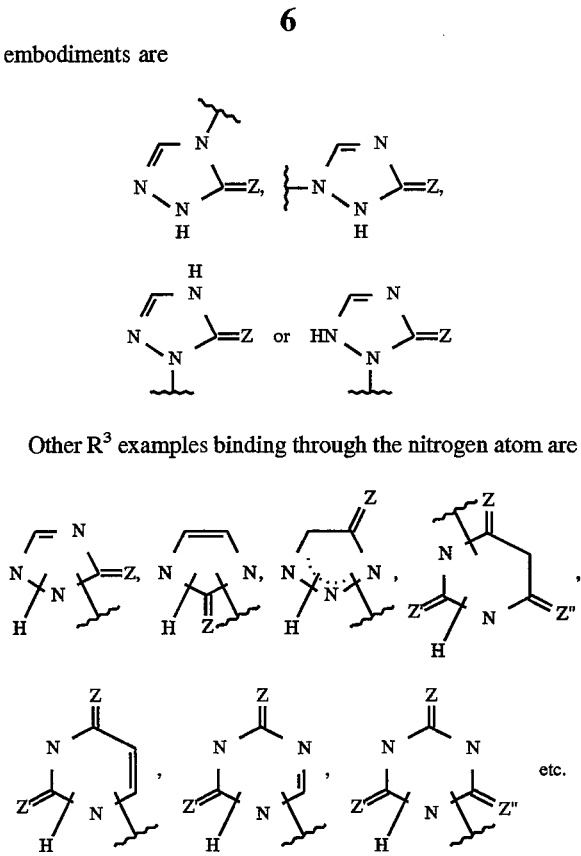

Other R³ examples binding through the nitrogen atom are

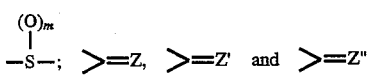

In the above groups, g stands for —CH$_2$—, —NR$^7$, oxygen atom, or

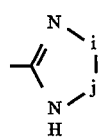

each stand for a carbonyl group, a thiocarbonyl group or an optionally oxidized sulfur atom (e.g., S, S(O), S(O)$_2$) (preferably, a carbonyl or thiocarbonyl group; more preferably, a carbonyl group); m stands for the integer 0, 1 or 2; R$^7$ stands for a hydrogen atom or an optionally substituted lower alkyl group (e.g. a lower (C$_{1-4}$) alkyl group (e.g. methyl, ethyl, propyl, isopropyl, butyl, sec-butyl, t-butyl)).

Preferable examples of R³ include 2,5-dihydro-5-oxo-1, 2,4-oxadiazole ring residue, 2,5-dihydro-5-thioxo-1,2,4-oxadiazole ring residue or 2,5-dihydro-5-oxo-1,2,4-thiadiazole ring residue having —NH or —OH group as proton donor and carbonyl group, thiocarbonyl group or sulfinyl group as proton acceptor simultaneously.

And, while the heterocyclic residue represented by R³ may form a condensed ring by connecting the substituents on the ring, it is preferably a 5- to 6- membered ring, more preferably a 5-membered heterocyclic residue. Especially, groups represented by the formula wherein i stands for —O— or —S—; j stands for >C=O, >C=S or >S(O)$_m$; m stands for the integer 0, 1 or 2 (in particular, 2,5-dihydro-5-oxo-1,2,4-oxadiazole-3-yl; 2,5- dihydro-5-thioxo-1,2,4-oxadiazole-3-yl; 2,5-dihydro-5-oxo-1,2,4-thiadiazole-3-yl) are preferable. $R^3$ can be substituted at the ortho, meta or para position, most preferably at the ortho position.

In addition, the above-mentioned heterocyclic residue ($R^3$) have the following tautomeric isomers:

In

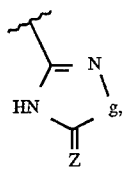

when Z=O, and g=O

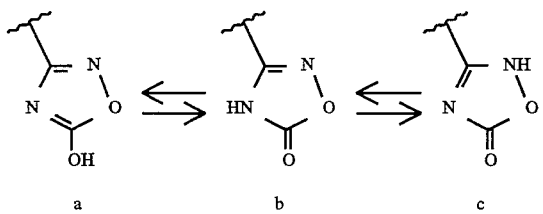

the three tautomeric isomers a, b and c exist.

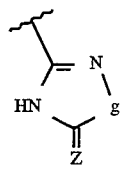

The heterocyclic residue represented by the above formula comprises all of these a, b and c.

Moreover, $R^3$ may be a carboxyl group, tetrazolyl group, trifluoromethanesulfonamide group (—NHSO$_2$CF$_3$), phosphate group, sulfonic group, cyano group, or lower ($C_{1-4}$) alkoxycarbonyl group; these groups each may be protected by an optionally substituted lower alkyl or acyl group. Any group capable of forming an anion biologically or physiologically (e.g. through biological reactions such as oxidation, reduction or hydrolysis caused by enzymes in the body) or chemically, or a group capable of changing thereto is acceptable.

As $R^3$, a tetrazolyl or carboxyl (preferably tetrazolyl) group optionally protected by an optionally substituted lower ($C_{1-4}$) alkyl (e.g., methyl, triphenylmethyl, methoxymethyl, ethoxymethyl, p-methoxybenzyl, p-nitrobenzyl, etc.) or acyl (e.g., lower ($C_{2-5}$) alkanoyl, benzoyl, etc.) group is preferable. $R^3$ can be replaced at the ortho, meta or para position, most preferably at the ortho position.

X stands for a covalent bond between the 2 phenyl rings or a spacer having a chain length of 1 to 2 atoms as the linear moiety between the adjoining phenylene group and phenyl group. Preferably, X is a covalent bond. The spacer having a chain length of 1 to 2 atoms may consist of a divalent chain in which the number of atoms composing the straight chain portion is either 1 or 2, and may have a side chain. For example, a lower ($C_{1-4}$) alkylene, —CO—, —O—, —S—, —NH—, —CO—NH—, —O—CH$_2$—, —S—CH$_2$—, —CH=CH—, etc. are listed.

n stands for the integer 1 or 2 (preferably 1).

The formula represented by the above-mentioned $R^3$, X and n:

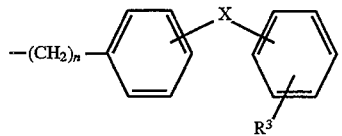

is preferably represented by the formula:

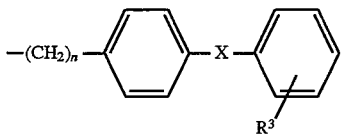

With respect to formula (I), the hydrocarbon residue for $R^2$ is exemplified by alkyl groups, alkenyl groups, alkynyl groups and cycloalkyl groups, with preference given to alkyl groups and alkenyl groups.

The alkyl group for $R^2$ is a lower alkyl group having about 1 to 8 carbon atoms, whether linear or branched, exemplified by methyl, ethyl, propyl, isopropyl, butyl, isobutyl, sec-butyl, t-butyl, pentyl, isopentyl, hexyl, heptyl and octyl.

The alkenyl group for $R^2$ is a lower alkenyl group having about 2 to 8 carbon atoms, whether linear or branched, exemplified by vinyl, propenyl, 2-butenyl, 3-butenyl, isobutenyl and 2-octenyl.

The alkinyl group for $R^2$ is a lower alkynyl group having about 2 to 8 carbon atoms, whether linear or branched, exemplified by ethynyl, 2-propynyl, 2-butynyl, 2-pentynyl and 2-octynyl.

The cycloalkyl group for $R^2$ is a lower cycloalkyl group having about 3 to 6 carbon atoms, exemplified by cyclopropyl, cyclobutyl, cyclopentyl and cyclohexyl.

The hydrocarbon residue for $R^2$ may be substituted with one or more substituents such as a hydroxyl group that may be substituted, an amino group that may be substituted (e.g., amino, dimethylamino, diethylamino, piperidino, morpholino), a halogen, a lower ($C_{1-6}$) alkoxy group, a lower ($C_{3-6}$) cycloalkoxy, a lower ($C_{1-6}$) alkylthio or a dioxolenyl (e.g., 5-methyl-2-oxo-1,3-dioxolen-4-yl).

The group represented by COOR$^2$ in formula (I) is preferably an optionally esterified carboxyl group.

Said optionally esterified carboxyl group as COOR$^2$ includes the group represented by the formula —CO—D [wherein D stands for a hydroxyl group or an optionally substituted alkoxy group {e.g., a lower ($C_{1-6}$) alkoxyl group whose alkyl portion is optionally substituted with a hydroxyl, optionally substituted amino (e.g., amino, dimethylamino, diethylamino, piperidino, molphorino, etc.), halogen, lower ($C_{1-6}$) alkoxy, lower ($C_{1-6}$) alkylthio or optionally substituted dioxolanyl (e.g., 5-methyl-2-oxo-1,3-dioxolane-4-yl, etc.) group, or the group represented by the formula —O—CH(R$^6$)—OCOR$^5$ [wherein R$^6$ stands for H, a lower ($C_{1-6}$) straight chain or branched alkyl group (e.g., methyl, ethyl, n-propyl, isopropyl, n-butyl, isobutyl, t-butyl, n-pentyl, isopentyl, neopentyl, etc.), a lower ($C_{2-6}$) straight chain or branched alkenyl group or a lower ($C_{3-8}$) cycloalkyl group (e.g., cyclopentyl, cyclohexyl, cycloheptyl, etc.); R$^5$ stands for a lower ($C_{1-6}$) straight chain or branched alkyl group (e.g., methyl, ethyl, n-propyl, isopropyl, n-butyl, isobutyl, sec-butyl, t-butyl, n-pentyl, isopentyl, neopentyl, etc.), a lower ($C_{2-6}$) straight chain or branched alkenyl group, a lower ($C_{3-8}$) cycloalkyl group (e.g., cyclopentyl, cyclohexyl, cycloheptyl, etc.), a lower ($C_{1-3}$) alkyl group substituted with $C_{3-8}$ cycloalkyl (e.g. cyclopentyl, cyclohexyl, cycloheptyl) or an optionally substituted aryl group such as phenyl group (e.g., benzyl, p-chlorobenzyl, phenetyl, cyclopentylmethyl, cyclohexylmethyl, etc.), a lower ($C_{2-3}$) alkenyl group optionally substituted with $C_{3-8}$ cycloalkyl or an optionally substituted aryl group such as phenyl (e.g., cinnamyl, etc. having alkenyl moiety such as vinyl, propenyl, allyl and isopropenyl, etc.), an aryl group such as optionally substituted phenyl (e.g., phenyl, p-tolyl, naphthyl, etc.), a lower ($C_{1-6}$) straight chain or branched alkoxy group (e.g., methoxy, ethoxy, nopropoxy, isopropoxy, n-butoxy, isobutoxy, sec-butoxy, t-butoxy, n-pentyloxy, isopentyloxy, neopentyloxy, etc.), a lower ($C_{2-8}$) straight chain or branched alkenyloxy group (e.g., allyloxy, isobutenyloxy, etc.), a lower ($C_{3-8}$) cycloalkyloxy group (e.g., cyclopentyloxy, cyclohexyloxy, cycloheptyloxy, etc.), a lower ($C_{1-3}$) alkoxy group substituted with a $C_{3-8}$ cycloalkyl (e.g., cyclopentyl, cyclohexyl, cycloheptyl, etc.) or an aryl group such as optionally substituted phenyl (e.g., benzyloxy, phenethyloxy, cyclopentylmethyloxy and cyclohexylmethyloxy having alkoxy moiety such as methoxy, ethoxy, n-propoxy and isopropoxy), a lower ($C_{2-3}$) lower alkenyloxy group substituted with a $C_{3-8}$ cycloalkyl (e.g., cyclopentyl, cyclohexyl, cycloheptyl, etc.) or an optionally substituted aryl group such as phenyl group (e.g., cinnamyloxy etc. having alkenyloxy moiety such as vinyloxy, propenyloxy, allyloxy, isopropenyloxy, etc.), or an optionally substituted aryloxy group such as phenoxy (e.g., phenoxy, p-nitrophenoxy, naphthoxy, etc.,)}].

The substituent $R^2$ is exemplified by hydrogen, methyl, ethyl, t-butyl, propyl, pivaloyloxymethyl, 1-(cyclohexyloxycarbonyloxy)ethyl, (5-methyl-2-oxo-1,3-dioxolen-4-yl)methyl, acetoxymethyl, propionyloxymethyl, n-butyryloxymethyl, isobutyryloxymethyl, 1-(ethoxycarbonyloxy)ethyl, 1-(acetoxy)ethyl, 1-(isobutyryloxy)ethyl, cyclohexylcarbonyloxymethyl, benzoyloxymethyl, cinnamyl and cyclopentylcarbonyloxymethyl.

$R^2$ in general formula (I) is preferably hydrogen or a lower ($C_{1-4}$) alkyl that may be substituted with a hydroxyl group, amino, halogen, lower ($C_{2-6}$) alkanoyloxy (e.g., acetoxy, pivaloyloxy), lower ($C_{4-7}$) cycloalkanoyloxy, (lower ($C_{1-6}$) alkoxy)carbonyloxy (e.g., methoxycarbonyloxy, ethoxycarbonyloxy), (lower ($C_{3-7}$) cycloalkoxy)carbonyloxy (e.g., cyclohexyloxycarbonyloxy), lower ($C_{1-6}$) alkoxy or lower ($C_{3-6}$) cycloalkoxy, with greater preference given to hydrogen and a lower ($C_{1-4}$) alkyl substituted with cyclohexyloxycarbonyloxy.

With respect to formula (I), ring A may have an additional substituent other than the group represented by $COOR^2$. Such additional substituents include halogens (e.g., F, Cl, Br), cyano, nitro, lower ($C_{1-4}$) alkyls, lower ($C_{1-4}$) alkoxys, amino groups that may be substituted (e.g., amino, N-lower ($C_{1-4}$) alkylaminos (e.g., methylamino), N,N-di-lower ($C_{1-4}$) alkylaminos (e.g., dimethylamino), N-arylaminos (e.g., phenylamino), cyclic aminos (e.g., morpholino, piperidino, piperazino, N-phenylpiperazino)), groups represented by the formula —CO—D'—[D' represents a hydroxyl group or a lower ($C_{1-4}$) alkoxy whose alkyl moiety may be substituted with a hydroxyl group, lower ($C_{1-4}$) alkoxy, lower ($C_{2-6}$) alkanoyloxy (e.g., acetoxy, pivaloyloxy), (lower ($C_{1-6}$) alkoxy)carbonyloxy (e.g., methoxycarbonyloxy, ethoxycarbonyloxy) or (lower ($C_{3-7}$) cycloalkoxy)carbonyloxy (e.g., cyclohexyloxycarbonyloxy) ], and tetrazolyl, trifluoromethanesulfonamide, phosphoric acid and sulfonic acid groups that may be protected by a lower ($C_{1-4}$) alkyl or acyl (e.g., lower ($C_{2-5}$) alkanoyl, benzoyl that may be substituted), with preference given to lower ($C_{1-4}$) alkyls and halogens. One or two of these substituents may be concurrently present at any position on the ring.

Among the compounds represented by the above mentioned formula (I), compounds represented by formula (I') are preferred:

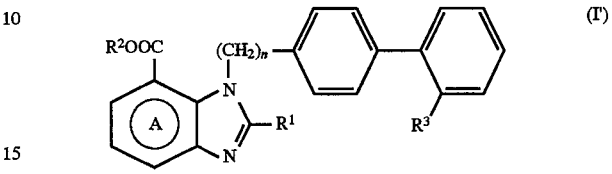

[wherein ring A stands for a benzene ring which may have another 1 or 2 substituents in addition to the group represented by $COOR^2$; $R^1$ stands for hydrogen or a lower ($C_{1-6}$) alkoxy (preferably lower ($C_{1-4}$) alkoxy); $R^2$ is hydrogen or a lower ($C_{1-4}$) alkyl that may be substituted with hydroxyl group, amino, halogen, a lower ($C_{2-6}$) alkanoyloxy (e.g. acetyloxy and pivaloyloxy, etc.), lower ($C_{4-7}$) cycloalkanoyloxy, (lower ($C_{1-6}$) alkoxy)carbonyloxy (e.g. methoxycarbonyloxy, ethoxycarbonyloxy), (lower ($C_{3-7}$) cycloalkoxy)carbonyloxy (e.g. cyclohexyloxycarbonyloxy) or a lower ($C_{1-4}$) alkoxy; $R^3$ stands for a tetrazolyl, carboxyl group or groups represented by the formula,

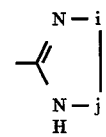

wherein i stands for —O— or —S—; j stands for >C=O, >C=S or >S(O)$_m$; and m is 0, 1 or 2, which are optionally protected with optionally substituted lower ($C_{1-4}$) alkyl (e.g. methyl, triphenylmethyl, methoxymethyl, acetyloxymethyl, methoxycarbonyloxymethyl, ethoxycarbonyloxymethyl, 1-(cyclohexyloxycarbonyloxy)ethyl and pivaloyloxymethyl, etc.) or an acyl group (e.g. a lower $C_{2-5}$ alkanoyl and benzoyl, etc.).; n is 1 or 2 (preferably 1).

In the formula (I'), ring A is a benzene ring which may have a substituent, in addition to the group $COOR^2$, such as a halogen (e.g., F, Cl, Br), lower ($C_{1-4}$) alkyl, lower ($C_{1-4}$) alkoxy, nitro, a group represented by the formula —CO—D', wherein D' represents a hydroxyl group or a lower ($C_{1-4}$) alkoxy whose alkyl moiety may be substituted with a hydroxyl group, lower ($C_{1-4}$) alkoxy, lower ($C_{2-6}$) alkanoyloxy (e.g., acetoxy, pivaloyloxy, etc.) or lower ($C_{1-6}$) alkoxycarbonyloxy (e.g., methoxycarbonyloxy, ethoxycarbonyloxy, cyclohexyloxycarbonyloxy), or an amino which may be substituted with a lower ($C_{1-4}$) alkyl (preferably a substituent such as a lower ($C_{1-4}$) alkyl or halogen). More preferably, A is a benzene ring which has no substituent in addition to the group represented by the formula $COOR^2$.

As the salt thereof, pharmaceutically acceptable salts are used, e.g., a salt with an inorganic base, organic base, inorganic acid, organic acid, or basic or acidic amino acid. Inorganic bases appropriate to form the salt include alkali metals such as sodium and potassium, alkali soil metals such as calcium and magnesium, aluminum and ammonium. Organic bases appropriate to form the salt include trimethylamine, triethylamine, pyridine, picoline, ethanolamine, diethanolamine, triethanolamine, dicyclohexylamine, and N,N'-dibenzylethylenediamine. Inorganic acids appropriate to form the salt include hydrochloric acid, hydroboric acid, nitric acid, sulfuric acid, and phosphoric acid. Organic acids appropriate to form the salt include formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid. Basic amino acids to form the salt include arginine, lysine and ornithine. Acidic amino acids to form the salt include aspartic acid and glutamic acid.

As an active ingredient of the present invention, the compounds described in the Examples of Japanese Published unexamined patent application (Kokai tokkyo koho) No. 364171/1992 and EP520423 are preferred.

The compounds represented by general formula (I) are, for instance, disclosed in Japanese Published unexamined patent application (Kokai tokkyo koho) Nos. 9373/1992 and 364171/1992, and EP520423, and can be manufactured as described in these publications.

For example, the compounds of formula (I) are as follows:
Methyl 2-ethoxy-1-[(2'-methoxycarbonylbiphenyl-4-yl) methyl]benzimidazole-7-carboxylate,
Ethyl 2-ethoxy-1-[[2'-(1H-tetrazol-5-yl)biphenyl-4-yl] methyl]benzimidazole-7-carboxylate,
2-Ethoxy-1-[[2'-(1H-tetrazol-5-yl)biphenyl-4-yl]methyl] benzimidazole-7-carboxylic acid,
Ethyl 2-propoxy-1-[[2'-(1H-tetrazol-5-yl)biphenyl-4-yl] methyl]benzimidazole-7-carboxylate,
2-Propoxy-1-[[2'-(1H-tetrazol-5-yl)biphenyl-4-yl]methyl] benzimidazole-7-carboxylic acid,
Ethyl 2-mercapto-1-[[2'-(1H-tetrazol-5-yl)biphenyl-4-yl] methyl]benzimidazole-7-carboxylate,
Ethyl 2-methylthio-1-[[2'-(1H-tetrazol-5-yl)biphenyl-4-yl] methyl]benzimidazole-7-carboxylate,
Ethyl 2-ethylthio-1-[[2'-(1H-tetrazol-5-yl)biphenyl-4-yl] methyl]benzimidazole-7-carboxylate,
Ethyl 2-propylthio-1-[[2'-(1H-tetrazol-5-yl)biphenyl-4-yl] methyl]benzimidazole-7-carboxylate,
2-Methylthio-1-[[2'-(1H-tetrazol-5-yl)biphenyl-4-yl] methyl]benzimidazole-7-carboxylic acid,
2-Ethylthio-1-[[2'-(1H-tetrazol-5-yl)biphenyl-4-yl]methyl] benzimidazole-7-carboxylic acid,
2-Propylthio-1-[[2'-(1H-tetrazol-5-yl)biphenyl-4-yl]methyl] benzimidazole-7-carboxylic acid,
Methyl 2-ethoxy-1-[[2'-(1H-tetrazol-5-yl)biphenyl-4-yl] methyl]benzimidazole-7-carboxylate,
Ethyl 2-ethylamino-1-[[2'-(1H-tetrazol-5-yl)biphenyl-4-yl] methyl]benzimidazole-7-carboxylate,
Ethyl 2-propylamino-1-[[2'-(1H-tetrazol-5-yl)biphenyl-4-yl]methyl]benzimidazole-7-carboxylate,
Pivaloyloxymethyl 2-ethoxy-1-[[2'-(1H-tetrazol-5-yl) biphenyl-4-yl]methyl]benzimidazole-7-carboxylate,
1-(Cyclohexyloxycarbonyloxy)ethyl 2-ethoxy-1-[[2'-(1H-tetrazol-5-yl)biphenyl-4-yl]methyl]benzimidazole-7-carboxylate,
Methyl 2-methoxy-1-[[2'-(1H-tetrazol-5-yl)biphenyl-4-yl] methyl]benzimidazole-7-carboxylate,
2-Methoxy-1-[[2'-(1H-tetrazol-5-yl )biphenyl-4-yl]methyl] benzimidazole-7-carboxylic acid,
2-Ethylamino-1-[[2'-(1H-tetrazol-5-yl)biphenyl-4-yl] methyl]benzimidazole-7-carboxylic acid,
2-Propylamino-1-[[2'-(1H-tetrazol-5-yl)biphenyl-4-yl] methyl]benzimidazole-7-carboxylic acid,
(5-Methyl-2-oxo-1,3-dioxolen-4-yl)methyl 2-ethoxy-1-[[2'-(1H-tetrazol-5-yl)biphenyl-4-yl]methyl]benzimidazole-7-carboxylate,
Acetoxymethyl 2-ethoxy-1-[[2'-(1H-tetrazol-5-yl)biphenyl-4-yl]methyl]benzimidazole-7-carboxylate,
Propionyloxymethyl 2-ethoxy-1-[[2'-(1H-tetrazol-5-yl) biphenyl-4-yl]methyl]benzimidazole-7-carboxylate,
Butyryloxymethyl 2-ethoxy-1-[[2'-(1H-tetrazol-5-yl) biphenyl-4-yl]methyl]benzimidazole-7-carboxylate,
Isobutyryloxymethyl 2-ethoxy-1-[[2'-(1H-tetrazol-5-yl) biphenyl-4-yl]methyl]benzimidazole-7-carboxylate,
1-(Ethoxycarbonyloxy)ethyl 2-ethoxy-1-[[2'-(1H-tetrazol-5-yl)biphenyl-4-yl]methyl]benzimidazole-7-carboxylate,
1-Acetoxyethyl 2-ethoxy-1-[[2'-(1H-tetrazol-5-yl)biphenyl-4-yl]methyl]benzimidazole-7-carboxylate,
1-(Isopropoxycarbonyloxy)ethyl 2-ethoxy-1-[[2'-(1H-tetrazol-5-yl)biphenyl-4-yl]methyl]benzimidazole-7-carboxylate,
2-Methylamino-1-[[2'-(1H-tetrazol-5-yl)biphenyl-4-yl] methyl]benzimidazole-7-carboxylic acid,
Cyclohexylcarbonyloxymethyl 2-ethoxy-1-[[2'-(1H-tetrazol-5-yl)biphenyl-4-yl]methyl]benzimidazole-7-carboxylate,
Benzoyloxymethyl 2-ethoxy-1-[[2'-(1H-tetrazol-5-yl) biphenyl-4-yl]methyl]benzimidazole-7-carboxylate,
(E)-Cinnamoyloxymethyl 2-ethoxy-1-[[2'-(1H-tetrazol-5-yl)biphenyl-4-yl]methyl]benzimidazole-7-carboxylate,
Cyclopentylcarbonyloxymethyl 2-ethoxy-1-[[2'-(1H-tetrazol-5-yl)biphenyl-4-yl]methyl]benzimidazole-7-carboxylate,
Pivaloyloxymethyl 2-ethylamino-1-[[2'-(1H-tetrazol-5-yl) biphenyl-4-yl]methyl]benzimidazole-7-carboxylate,
1-(Cyclohexyloxycarbonyloxy)ethyl 2-ethylamino-1-[[2'-(1H-tetrazol-5-yl)biphenyl-4-yl]methyl]benzimidazole-7-carboxylate,
Methyl 2-allyloxy-1-[[2'-(1H-tetrazol-5-yl)biphenyl-4-yl] methyl]benzimidazole-7-carboxylate,
Methyl 2-butoxy-1-[[2'-(1H-tetrazol-5-yl)biphenyl-4-yl] methyl]benzimidazole-7-carboxylate,
Methyl 2-butylamino-1-[[2'-(1H-tetrazol-5-yl)biphenyl-4-yl]methyl]benzimidazole-7-carboxylate,
Methyl 1-[[2'-(1H-tetrazol-5-yl)biphenyl-4-yl]methyl]-2-morpholinobenzimidazole-7-carboxylate,
Methyl 1-[[2'-(1H-tetrazol-5-yl)biphenyl-4-yl]methyl]-2-piperidinobenzimidazole-7-carboxylate,
Methyl 2-ethylmethylamino-1-[[2'-(1H-tetrazol-5-yl) biphenyl-4-yl]methyl]benzimidazole-7-carboxylate,
2-Piperidino-1-[[2'-(1H-tetrazol-5-yl)biphenyl-4-yl]methyl] benzimidazole-7-carboxylic acid,
2-Morpholino-1-[[2'-(1H-tetrazol-5-yl)biphenyl-4-yl] methyl]benzimidazole-7-carboxylic acid,
2-(N-Ethylmethylamino)-1-[[2'-(1H-tetrazol-5-yl)biphenyl-4-yl]methyl]benzimidazole-7-carboxylic acid,
2-Butylamino-1-[[2'-(1H-tetrazol-5-yl)biphenyl-4-yl] methyl]benzimidazole-7-carboxylic acid,
2-Ethoxy-1-[[2'-carboxybiphenyl-4-yl]methyl] benzimidazole-7-carboxylic acid,
Methyl 2-ethylamino-1-[[2'-(1H-tetrazol-5-yl)biphenyl-4-yl]methyl]benzimidazole-7-carboxylate,
Methyl 1-[[2'-(1H-tetrazol-5-yl)biphenyl-4-yl]methyl]-2-(2,2,2-trifluoroethoxy)benzimidazole-7-carboxylate,
1-[[2'-(1H-tetrazol-5-yl)biphenyl-4-yl]methyl]-2-(2,2,2-trifluoroethoxy)benzimidazole-7-carboxylic acid,
2-Ethoxy-1-[[2'-(2,5-dihydro-5-oxo-1,2,4-oxadiazol-3-yl) biphenyl-4-yl]methyl]benzimidazole-7-carboxylic acid,
Methyl 2-ethoxy-1-[[2'-(2,5-dihydro-5-oxo-1,2,4-oxadiazol-3-yl)biphenyl-4-yl]methyl]benzimidazole-7-carboxylate,
Methyl 2-butyl-1-[[2'-(2-oxo-3H-1,2,3,5-oxathiadiazol-4-yl)biphenyl]methyl]benzimidazole-7-carboxylate, Methyl 2-ethoxy-1-[[2'-(2-oxo-3H-1,2,3,5-oxathiadiazol-4-yl)biphenyl]methyl]benzimidazole-7-carboxylate, 1-(Cyclohexyloxycarbonyloxy)ethyl 2-ethoxy-1-[[2'-(2,5-dihydro-5-oxo-1,2,4-oxadiazol-3-yl)biphenyl-4-yl]methyl]benzimidazole-7-carboxylate, 2-Butyl-1-[[2'-(2,3-dihydro-2-oxo-1,3,4-oxadiazol-5-yl)biphenyl-4-yl]methyl]benzimidazole-7-carboxylic acid, Methyl 2-butyl-1-[[2'-(2,3-dihydro-2-oxo-1,3,4-oxadiazol-5-yl)biphenyl-4-yl]methyl]benzimidazole-7-carboxylate, Acetoxymethyl 1-[[2'-(4-acetoxymethyl-4,5-dihydro-5-oxo-4H-1,2,4-oxadiazol-3-yl)biphenyl-4-yl]methyl-2-ethoxybenzimidazole-7-carboxylate, Acetoxymethyl 2-ethoxy-1-[[2'-(2,5-dihydro-5-oxo-1,2,4-oxadiazol-3-yl)biphenyl-4-yl]methyl]benzimidazole-7-carboxylate, 1-[[2'-(4-Acetoxymethyl-4,5-dihydro-5-oxo-4H-1,2,4-oxadiazol-3-yl)biphenyl-4-yl]methyl]-2-ethoxybenzimidazole-7-carboxylic acid, 1-[[2'-(2,5-Dihydro-5-oxo-1,2,4-oxadiazol-3-yl)biphenyl-4-yl]methyl]-2-propylbenzimidazole-7-carboxylic acid, Methyl 1-[[2'-(2,5-dihydro-5-oxo-1,2,4-oxadiazol-3-yl)biphenyl-4-yl)methyl]-2-propylbenzimidazol-7-carboxylate, 2-Ethyl-1-[[2'-(2,5-dihydro-5-oxo-1,2,4-oxadiazol-3-yl)-biphenyl-4-yl)methyl]benzimidazole-7-carboxylic acid, 2-Cyclopropyl-1-[[2'-(2,5-dihydro-5-oxo-1,2,4-oxadiazol-3-yl )biphenyl-4-yl)methyl]benzimidazole-7-carboxylic acid, Methyl 2-cyclopropyl-1-[[2'-(2,5-dihydro-5-oxo-1,2,4-oxadiazol-3-yl)biphenyl-4-yl)methyl]benzimidazole-7-carboxylate, 2-Butyl-[[2'-(2,5-dihydro-5-oxo-1,2,4-oxadiazol-3-yl)biphenyl-4-yl)methyl]benzimidazole-7-carboxylic acid, 1-[[2'-(2,5-dihydro-5-oxo-1,2,4-oxadiazol-3-yl)biphenyl-4-yl)methyl]-2-propylthiobenzimidazole-7-carboxylic acid, Methyl 1-[[2'-(2,5-dihydro-5-oxo-1,2,4-oxadiazol-3-yl)biphenyl-4-yl)methyl]-2-propylthiobenzimidazole-7-carboxylate, 1-[[2'-(2,5-Dihydro-5-oxo-1,2,4-oxadiazol-3-yl)biphenyl-4-yl)methyl]-2-methoxybenzimidazole-7-carboxylic acid, Methyl 1-[[2'-(2,5-dihydro-5-oxo-1,2,4-oxadiazol-3-yl)biphenyl-4-yl)methyl]-2-methoxybenzimidazole-7-carboxylate, 1-[[2'-(2,5-Dihydro-5-oxo-1,2,4-oxadiazol-3-yl)biphenyl-4-yl)methyl]-2-propoxybenzimidazole-7-carboxylic acid, Methyl 1-[[2'-(2,5-dihydro-5-oxo-1,2,4-oxadiazol-3-yl)biphenyl-4-yl)methyl]-2-propoxybenzimidazole-7-carboxylate, 2-Ethylthio-1-[[2'-(2,5-dihydro-5-oxo-1,2,4-oxadiazol-3-yl)biphenyl-4-yl)methyl]benzimidazole-7-carboxylic acid, Methyl 2-ethylthio-1-[[2'-(2,5-dihydro-5-oxo-1,2,4-oxadiazol-3-yl)biphenyl-4-yl)methyl]benzimidazole-7-carboxylate, 1-[[2'-(2,5-Dihydro-5-oxo-1,2,4-oxadiazol-3-yl)biphenyl-4-yl)methyl]-2-methylthiobenzimidazole-7-carboxylic acid, Methyl 1-[[2'-(2,5-dihydro-5-oxo-1,2,4-oxadiazol-3-yl)biphenyl-4-yl)methyl]-2-methylthiobenzimidazole-7-carboxylate, Dipotassium salt of 2-Ethoxy-1-[[2'-(5-oxide-1,2,4-oxadiazol-3-yl)biphenyl-4-yl)methyl]benzimidazole-7-carboxylic acid, Disodium salt of 2-ethoxy-1-[[2'-(5-oxide-1,2,4-oxadiazol-3-yl)biphenyl-4-yl)methyl]benzimidazole-7-carboxylic acid, Methyl 2-ethoxy-1-[[2'-(2,5-dihydro-5-oxo-1,2,4-thiadiazol-3-yl)biphenyl-4-yl)methyl]benzimidazole-7-carboxylate, 2-Ethoxy-1-[[2'-(2,5-dihydro-5-oxo-1,2,4-thiadiazol-3-yl)biphenyl-4-yl)methyl]benzimidazole-7-carboxylic acid, Methyl 2-ethoxy-1-[[2'-(2,5-dihydro-5-thioxo-1,2,4-oxadiazol-3-yl)biphenyl-4-yl]methyl]benzimidazole-7-carboxylate, Methyl 2-butyl-1-[[2'-(2,5-dihydro-5-thioxo-1,2,4-oxadiazol-3-yl)biphenyl-4-yl]methyl]benzimidazol-7-carboxylate, 2-Butyl-1-[[2'-(2,5-dihydro-5-thioxo-1,2,4-oxadiazol-3-yl)biphenyl-4-yl]methyl]benzimidazole-7-carboxylic acid, Methyl 2-butyl-1-[[2'-(2,5-dihydro-5-oxo-1,2,4-thiadiazol-3-yl]biphenyl-4-yl]methyl]benzimidazole-7-carboxylate, 2-Butyl-1-[[2'-(2,5-dihydro-5-oxo-1,2,4-thiadiazol-3-yl] biphenyl-4-yl]methyl]benzimidazole-7-carboxylic acid, Methyl 2-ethyl-1-[[2'-(2,5-dihydro-5-oxo-1,2,4-thiadiazol-3-yl]biphenyl-4-yl]methyl]benzimidazole-7-carboxylate, 2-Ethyl-1-[[2'-(2,5-dihydro-5-oxo-1,2,4-thiadiazol-3-yl] biphenyl-4-yl]methyl]benzimidazole-7-carboxylic acid, Methyl 2-ethyl-1-[[2'-(2,5-dihydro-5-thioxo-1,2,4-oxadiazol-3-yl)biphenyl-4-yl]methyl]benzimidazole-7-carboxylate, Methyl 1-[[2'-(2,5-dihydro-5-thioxo-1,2,4-oxadiazol-3-yl)biphenyl-4-yl]methyl]-2-propylbenzimidazole-7-carboxylate, Methyl 1-[[2'-(2,5-dihydro-5-oxo-1,2,4-thiadiazol-3-yl)biphenyl-4-yl]methyl]-2-propylbenzimldazole-7-carboxylate, 1-[[2'-(2,5-dihydro-5-oxo-1,2,4-thiadiazol-3-yl)biphenyl-4-yl]methyl]-2-methoxybenzimidazole-7-carboxylic acid, 1-[[2'-(2,5-dihydro-5-oxo-1,2,4-thiadiazol-3-yl)biphenyl-4-yl]methyl]-2-propoxybenzimidazole-7-carboxylic acid, 1-[[2'-(2,5-dihydro-5-oxo-1,2,4-thiadiazol-3-yl)biphenyl-4-yl]methyl]-2-methylbenzimidazole-7-carboxylic acid, 2-cyclopropyl-1-[[2'-(2,5-dihydro-5-oxo-1,2,4-thiadiazol-3-yl)biphenyl-4-yl]methyl]benzimidazole-7-carboxylic acid, The compound of the present invention or salt thereof, represented by formula (I), can be used as a pharmaceutical at low toxicity in animals (warm-blooded animals), particularly mammals (e.g., human, dogs, rabbits, rats, mice). It can be advantageously used as an ocular hypotensive agent possessing excellent action for lowering intraocular pressure in the prophylaxis or treatment of glaucoma and diseases caused by ocular hypertension (e.g. glaucoma).

The ocular hypotensive agent exhibits excellent action for lowering intraocular pressure without side effects (e.g., ocular irritation, conjunctival hyperemia).

The compound (or salt thereof) represented by general formula (I) can be orally or non-orally used. It can be used as a pharmaceutical composition or preparation (e.g., powders, granules, tablets, pills, capsules, injectable preparations, syrups, emulsions, elixirs, suspensions, solutions), in which at least one compound of the present invention may be used singly or in combination with pharmaceutically acceptable carriers (e.g., excipients, shaping agents and/or diluents).

Pharmaceutical compositions can be prepared as pharmaceutical preparations by ordinary methods. Solid dosage forms for oral administration include the above-mentioned ones such as powders, granules, tablets, pills and capsules. In these dosage forms, the active ingredient compound may be mixed with at least one additive such as sucrose, lactose, cellulose sugar, mannitol, maltitol, dextran, starch, agar, alginate, chitin, chitosan, pectin, gum tragacanth, gum arabic, gelatin, collagen, casein, albumin, synthetic or semi-synthetic polymer or glyceride. Such dosage forms may contain additional additives as usual, including inert diluents, lubricants such as magnesium stearate, preservatives such as paraben and sorbic acid, antioxidants such as ascorbic acid, a-tocopherol and cysteine, disintegrating agents, binders, thickening agents, buffers, sweeteners, flavoring agents and perfumes. Tablets and pills may be produced with enteric coating. Liquid dosage forms for oral administration include pharmaceutically acceptable emulsions, syrups, elixirs, suspensions and solutions, which may contain inert diluents, such as water, in common use in relevant fields.

In the present specification, "non-oral" includes injection, rectal administration and local administration. Methods of injection include subcutaneous injection, intravenous injection, intramuscular injection, intraperitoneal injection and drip infusion. Injectable preparations, e.g., aqueous or oily suspensions for aseptic injection, can be prepared by methods known in relevant fields, using an appropriate dispersing agent or wetting agent and a suspending agent. The aseptic injectable preparation thus obtained may be an aseptically injectable solution or suspension in a diluent or solvent which permits non-toxic non-oral administration, such as an aqueous solution. Acceptable vehicles or solvents include water, Ringer's solution and isotonic saline. It is also possible to use aseptic non-volatile oils in common use as solvents or suspending media. For this purpose any non-volatile oil or fatty acid can be used, including natural, synthetic or semi-synthetic fatty oils or acids, and natural, synthetic or semi-synthetic toorio- or di- or tri-glycerides.

Suppositories for rectal administration may be produced as a mixture of the drug and an appropriate non-irritative shaping agent that is solid at normal temperatures and liquid at intestinal temperatures and melts and releases the drug in the rectum, such as cacao butter or polyethylene glycol.

The ocular hypotensive agent of the present invention is preferably used for local administration to the eye. For local administration to the eye, the ocular hypotensive agent of the present invention is preferably used in the form of eyedrops or ophthalmic ointment. The eyedrops may be aqueous or non-aqueous, and may be in solution or suspension. It can also be used as dispersed in, or adsorbed to, an ophthalmic ointment, gel or sustained-release polymer.

The aqueous eyedrops may contain various additives in common use in ophthalmic solutions, such as isotonizing agents, buffers, pH regulators, preservatives and chelating agents. Isotonizing agents include sodium chloride, mannitol, sorbitol and glycerol; buffers include phosphates, boric acid, acetates and citrates; pH regulators include hydrochloric acid, acetic acid and sodium hydroxide; preservatives include p-oxybenzoates, benzalkonium chloride, chlorhexidine, benzyl alcohol, sorbic acid or salt thereof, thimerosal and chlorobutanol; chelating agents include sodium edetate, sodium citrate and condensed sodium phosphate. The aqueous eyedrops may incorporate viscolyzer and/or suspending agents. Viscolyzer and/or suspending agents include methyl cellulose, carmellose or salts, hydroxyethyl cellulose, sodium alginate, carboxyvinyl polymer, polyvinyl alcohol and polyvinylpyrrolidone. Surfactants such as polyethylene glycol, propylene glycol, polyoxyethylene hydrogenated castor oil and polysorbate 80 may be incorporated in the aqueous eyedrops.

When the ocular hypotensive agent of the present invention is prepared as an aqueous ophthalmic suspension, the above-mentioned polymeric thickening agents, surfactants etc. can be used as appropriate.

When the ocular hypotensive agent of the present invention is prepared as a non-aqueous ophthalmic solution, vegetable oils such as castor oil, olive oil, sesame oil and soybean oil, and other solvents such as liquid paraffin, propylene glycol and β-octyldodecanol can be used as appropriate.

When the ocular hypotensive agent of the present invention is prepared as a non-aqueous ophthalmic suspension, thixotropic colloids such as aluminum monostearate can be used as appropriate.

The eyedrops of the present invention may have any pH, as long as it falls within the normally used range of pH; it is recommended that pH be within the range of 4.0–9.0, preferably 5.0–8.0.

When the ocular hypotensive agent of the present invention is prepared as an ophthalmic ointment, petrolatum, plastibase, liquid paraffin etc. can be used as ointment bases, as appropriate.

When the ocular hypotensive agent of the present invention is prepared as an ophthalmic gel, carboxyvinyl polymer, methyl cellulose, sodium alginate, hydroxypropyl cellulose, ethylene-maleic anhydride polymer etc. can be used as bases, as appropriate.

The dose for a particular patient is determined according to age, body weight, general health status, sex, dietary status, administration time, method of administration, excretion rate, drug combination, the severity of the illness being treated and other factors.

The compound (or salt thereof) represented by formula (I) can be safely used at low toxicity. The daily dose, varying depending on the patient's condition, body weight, type of compound, route of administration and other factors, is normally about 0.01 to 150 mg/person/day, preferably 0.1 to 100 mg/person/day for oral administration, and about 0.01 to 50 mg/person/day, preferably 0.01 to 20 mg/person/day for non-oral routes such as subcutaneous, intravenous, intramuscular and rectal administration.

When the ocular hypotensive agent of the present invention is used as eyedrops, it is desirable that the concentration be normally about 0.001–10 w/v %, preferably about 0.01–5 w/v %, more preferably about 0.1–2 w/v % and that it be administered in one to several drops, preferably one to two, (the mount of one drop is about 50 µl), about 3 to 6 times, preferably about 4 to 5 times, a day in adult patients. When the ocular hypotensive agent of the present invention is used as an ophthalmic ointment, it is desirable that the concentration be normally about 0.001–10 w/w %, preferably about 0.01–5 w/w %, more preferably about 0.1–2 w/w %, and that it be instilled into the eonjunctival sac in an amount of about 0.1 to 0.2 g, about 1 to 4 times, a day.

The ocular hypotensive agent of the present invention may be formulated with one or more ocular hypotensive agents other than the compound (or salt thereof) represented by general formula (I), as long as the accomplishment of the object of the present invention is not interfered with.

The ocular hypotensive agent of the present invention may also be formulated using one or more components having pharmacological actions other than ocular hypotensive action, as long as the accomplishment of the object of the invention is not interfered with.

The present invention is hereinafter described in more detail by means of the following experimental examples and working examples to demonstrate the effect of the invention, but the examples are not to be construed as limiting the scope of the invention.

EXPERIMENTAL EXAMPLES

EXPERIMENTAL EXAMPLE 1

The action for lowering intraocular pressure in rabbits

Methods

Male Japanese albino and pigmented rabbits having no anterior ocular abnormalities were used. One eye received 50 μl of the test drug, the other eye 50 μl of physiological saline as a control. Changes over time in ocular tension were measured. Ocular tension was measured for both eyes using a Pneumatonograph (produced by Alcon) before and 30 minutes and/or 1 hour after instillation. The results are given in Table 1. The test drug was (±)-1-(cyclohexyloxycarbonyloxy)ethyl 2-ethoxy-1-[[2'-(1H-tetrazol-5-yl)biphenyl-4-yl]methyl]-1H-benzimidazole-7-carboxylate (hereinafter referred to as Compound 1) as suspended in physiological saline or 0.1 w/v % polysorbate 80 to concentrations of 0.1, 0.5 and 1.0 w/v %. Also performed periodically were macroscopic observation of the anterior ocular segment and measurement of pupil diameter.

Results

TABLE 1

The action for lowering intraocular pressure in Japanese albino rabbits

| Treatment | Concentration (w/v %) | n | Before Instillation | 30 minutes after Instillation | Difference |
|---|---|---|---|---|---|
| Control (physiological saline) | | 5 | 17.5 ± 0.81 | 17.4 ± 0.80 | −0.1 |
| Compound 1 | 1.0 | 5 | 18.7 ± 0.44 | 15.0 ± 0.47* | −3.7 |
| Control (physiological saline) | | 5 | 17.7 ± 1.24 | 17.5 ± 1.24 | −0.2 |
| Compound 1 | 0.5 | 5 | 18.2 ± 0.60 | 16.0 ± 0.76 | −2.2 |
| Control (physiological saline) | | 5 | 17.8 ± 0.62 | 18.0 ± 0.84 | +0.2 |
| Compound 1 | 0.1 | 5 | 17.8 ± 0.80 | 16.3 ± 1.16 | −1.5 |

*$p < 0.05$ vs intraocular pressure before instillation

As shown in Table 1, in the eyes instilled with compound 1 suspension (suspended in physiological saline), ocular tension fell dose-dependently by 30 minutes after instillation. At all concentrations used, no macroscopic abnormalities were noted in the anterior ocular segment of rabbits after instillation. Nor was there any change in pupil diameter.

TABLE 2

The action for lowering intraocular pressure in pigmented rabbits

| Treatment | Concentration (w/v %) | n | Before Instillation | Intraocular Pressure (mmHg) 30 minutes after Instillation | 1 hour after instillation |
|---|---|---|---|---|---|
| Control (physiological saline) | | 7 | 24.1 ± 0.39 | 23.6 ± 0.3 | 23.8 ± 0.34 |
| Compound 1 | 1.0 | 7 | 24.0 ± 0.29 | 21.9 ± 0.81 | 21.4 ± 0.43** |
| Control (physiological saline) | | 6 | 24.1 ± 0.33 | 23.6 ± 0.42 | 24.0 ± 0.5 |
| Compound 1 | 0.1 | 6 | 24.3 ± 0.25 | 22.0 ± 0.39* | 23.6 ± 0.33 |

*$p < 0.05$ vs intraocular pressure before instillation
**$p < 0.001$ vs intraocular pressure before instillation As shown in Table 2, in the eyes instilled with 0.1 w/v % and 1.0 w/v % compound 1 suspensions (suspended in 0.1 w/v % polysorbate 80) fell greatly at minutes and one hour after instillation, respectively. At all concentrations used, no macroscopic abnormalities were noted in the anterior ocular segment of rabbits after instillation. Nor was there any change in pupil diameter. Compound 1 proved a clinically safe drug exhibiting excellent action for lowering intraocular pressure.

EXPERIMENTAL EXAMPLE 2

Acute Toxicity Test

Compound 1: (±)-1-(cyclohexyloxycarbonyloxy)ethyl 2-ethoxy-1-[[2'-(1H-tetrazol-5-yl)biphenyl-4-yl]methyl]-1H-benzimidazole-7-carboxylate The $LD_{50}$ of compound 1 exceeded 2,000 mg/kg, as of single oral administration, in 4-week-old Jcl:ICR mice (males, females) and 5-week-old Jcl:Wistar rats (males, females).

EXAMPLES

EXAMPLE 1

| Ophthalmic suspension | |
|---|---|
| (1) (±)-1-(cyclohexyloxycarbonyloxy)ethyl 2-ethoxy-1-[[2'-(1H-tetrazol-5-yl)biphenyl-4-yl]methyl]-1H-benzimidazole-7-carboxylate (compound 1) | 1.0 g |
| (2) Sodium dihydrogen phosphate | 0.2 g |
| (3) Sodium chloride | 0.9 g |
| (4) Polysorbate 80 | 0.1 g |
| (5) Benzalkonium chloride | 0.005 g |

| Ophthalmic suspension | |
|---|---|
| 6) Sodium edetate | 0.01 g |
| 7) 1 N sodium hydroxide | q.s. |
| 8) Sterile purified water | Total 100 ml |

After components (2), (3), (4), (5) and (6) are dissolved in about 80 ml of component (8), component (7) is added to obtain pH 7. Component (8) is added to a total quantity of 100 ml, and the solution is filtered through a 0.2 μm membrane filter. Component (1), previously sterilized, is suspended in the solution to yield an ophthalmic suspension.

EXAMPLE 2

| Oily ophthalmic solution | |
|---|---|
| (1) Compound 1 | 2.0 g |
| (2) Castor oil | q.s. |
| | Total 100 ml |

Component (1) is added to component (2), previously sterilized, to yield an oily ophthalmic solution.

EXAMPLE 3

| Ophthalmic ointment | |
|---|---|
| (1) Compound 1 | 5.0 g |
| (2) Liquid paraffin | 5.0 g |
| (3) Plastibase | q.s. |
| | Total 100 g |

After components (2) and (3) are thermally sterilized, components (1) and (2) are thoroughly kneaded, and component (3) is added to a total quantity of 100 g, followed by thorough kneading, to yield an ophthalmic ointment.

EXAMPLE 4

| Gel | |
|---|---|
| (1) Compound 1 | 1.0 g |
| (2) Carboxyvinyl polymer | 0.5 g |
| (3) Benzalkonium chloride | 0.01 g |
| (4) 1 N sodium hydroxide | q.s. |
| (5) Sterile purified water | Total 100 g |

After component (3) is dissolved in about 80 g of component (5), the solution is filtered through a 0.2 μm membrane filter. Component (1), previously sterilized, is suspended in the solution, after which component (2), previously sterilized, is dissolved in the suspension, while the suspension is stirred vigorously. After component (4) is added to obtain pH 7, component (5) is added to a total quantity of 100 g, to yield a gel.

EXAMPLE 5

| Ophthalmic suspension | |
|---|---|
| (1) 2-ethoxy-1-[[2'-(2,5-dihydro-5-oxo-1,2,4- | 1.0 g |

| Ophthalmic suspension | |
|---|---|
| oxadiazol-3-yl)biphenyl-4-yl]methyl]-1H-benzimidazole-7-carboxylic acid | |
| (2) Sodium dihydrogen phosphate | 0.2 g |
| (3) Sodium chloride | 0.9 g |
| (4) Polysorbate 80 | 0.1 g |
| (5) Benzalkonium chloride | 0.005 g |
| (6) Sodium edetate | 0.01 g |
| (7) 1 N sodium hydroxide | q.s. |
| (8) Sterile purified water | Total 100 ml |

After components (2), (3), (4), (5) and (6) are dissolved in about 80 ml of component (8), component (7) is added to obtain pH 7. Component (8) is added to a total quantity of 100 ml, and the solution is filtered through a 0.2 μm membrane filter. Component (1), previously sterilized, is suspended in the solution to yield an ophthalmic suspension.

EXAMPLE 6

| Oily ophthalmic solution | |
|---|---|
| (1) 2-ethoxy-1-[[2'-(2,5-dihydro-5-oxo-1,2,4-oxadiazol-3-yl)biphenyl-4-yl]methyl]-1H-benzimidazole-7-carboxylic acid | 2.0 g |
| (2) Castor oil | q.s. |
| | Total 100 ml |

Component (1) is added to component (2), previously sterilized, to yield an oily ophthalmic solution.

EXAMPLE 7

| Ophthalmic ointment | |
|---|---|
| (1) 2-ethoxy-1-[[2'-(2,5-dihydro-5-oxo-1,2,4-oxadiazol-3-yl)biphenyl-4-yl]methyl]-1H-benzimidazole-7-carboxylic acid | 5.0 g |
| (2) Liquid paraffin | 5.0 g |
| (3) Plastibase | q.s. |
| | Total 100 g |

After components (2) and (3) are thermally sterilized, components (1) and (2) are thoroughly kneaded, and component (3) is added to a total quantity of 100 g, followed by thorough kneading, to yield an ophthalmic ointment.

EXAMPLE 8

| Gel | |
|---|---|
| (1) 2-ethoxy-1-[[2'-(2,5-dihydro-5-oxo-1,2,4-oxadiazol-3-yl)biphenyl-4-yl]methyl]-1H-benzimidazole-7-carboxylic acid | 1.0 g |
| (2) Carboxyvinyl polymer | 0.5 g |
| (3) Benzalkonium chloride | 0.01 g |
| (4) 1 N sodium hydroxide | q.s. |
| (5) Sterile purified water | Total 100 g |

After component (3) is dissolved in about 80 g of component (5), the solution is filtered through a 0.2 μm membrane filter. Component (1), previously sterilized, is suspended in the solution, after which component (2), previously sterilized, is dissolved in the suspension, while stirring the suspension vigorously. After component (4) is added to obtain pH 7, component (5) is added to a total quantity of 100 g, to yield a gel.

EXAMPLE 9

| Capsules | |
|---|---|
| (1) 2-ethoxy-1-[[2'-(1H-tetrazol-5-yl)biphenyl-4-yl]methyl]-1H-benzimidazole-7-carboxylic acid | 10 mg |
| (2) Lactose | 90 mg |
| (3) Microcrystalline cellulose | 70 mg |
| (4) Magnesium stearate | 10 mg |
| Total 180 mg per capsule | |

Components (1), (2) and (3) and a half portion of component (4) are mixed and granulated. To these granules, the remaining portion of component (4) is added, and the whole mixture is packed in a gelatin capsule.

EXAMPLE 10

| Tablets | |
|---|---|
| (1) 2-ethoxy-1-[[2'-(1H-tetrazol-5-yl)biphenyl-4-yl]methyl]-1H-benzimidazole-7-carboxylic acid | 10 mg |
| (2) Lactose | 35 mg |
| (3) Corn starch | 150 mg |
| (4) Microcrystalline cellulose | 30 mg |
| (5) Magnesium stearate | 5 mg |
| Total 230 mg per tablet | |

Components (1), (2) and (3), a two-thirds portion of component (4) and a half portion of component (5) are mixed and granulated. To these granules, the remaining portions of components (4) and (5) are added, and the whole mixture is tableted by compressive tableting.

EXAMPLE 11

| Injectable preparation | |
|---|---|
| (1) 2-methylthio-1-[[2'-(1H-tetrazol-5-yl)biphenyl-4-yl]methyl]-1H-benzimidazole-7-carboxylic acid disodium salt | 10 mg |
| (2) Inositol | 100 mg |
| (3) Benzyl alcohol | 20 mg |
| Total 130 mg per ampule | |

Components (1), (2) and (3) are dissolved in distilled water for injection to a total quantity of 2 ml, and the solution is packed in an ampoule. The entire procedure is performed aseptically.

EXAMPLE 12

| Capsules | |
|---|---|
| (1) Compound I | 10 mg |
| (2) Lactose | 90 mg |
| (3) Microcrystalline cellulose | 70 mg |
| (4) Magnesium stearate | 10 mg |
| Total 180 mg per capsule | |

Components (1), (2) and (3) and a half portion of component (4) are mixed and granulated. To these granules, the remaining portion of component (4) is added, and the whole mixture is packed in a gelatin capsule.

EXAMPLE 13

| Tablets | |
|---|---|
| (1) Compound I | 10 mg |
| (2) Lactose | 35 mg |
| (3) Corn starch | 150 mg |
| (4) Microcrystalline cellulose | 30 mg |
| (5) Magnesium stearate | 5 mg |
| Total 230 mg per tablet | |

Components (1), (2) and (3), a two-thirds portion of component (4) and a half portion of component (5) are mixed and granulated. To these granules, the remaining portions of components (4) and (5) are added, and the whole mixture is tableted by compressive tableting.

EXAMPLE 14

| Injectable preparation | |
|---|---|
| (1) 2-ethoxy-1-[[2'-(1H-tetrazol-5-yl)biphenyl-4-yl]methyl]-1H-benzimidazole-7-carboxylic acid disodium salt | 10 mg |
| (2) Inositol | 100 mg |
| (3) Benzyl alcohol | 20 mg |
| Total 130 mg per ampule | |

Components (1), (2) and (3) are dissolved in distilled water for injection to a total quantity of 2 ml, and the solution is packed in an ampoule. The entire procedure is performed aseptically.

EXAMPLE 15

| Capsules | |
|---|---|
| (1) 2-butyl-1-[[2'-(1H-tetrazol-5-yl)biphenyl-4-yl]methyl]-1H-benzimidazole-7-carboxylic acid | 10 mg |
| (2) Lactose | 90 mg |
| (3) Microcrystalline cellulose | 70 mg |
| (4) Magnesium stearate | 10 mg |
| Total 180 mg per capsule | |

Components (1), (2) and (3) and a half portion of component (4) are mixed and granulated. To these granules, the remaining portion of component (4) is added, and the whole mixture is packed in a gelatin capsule.

EXAMPLE 16

| Tablets | |
|---|---|
| (1) 2-butyl-1-[[2'-(1H-tetrazol-5-yl)biphenyl-4-yl]methyl]benzimidazole-7-carboxylic acid | 10 mg |
| (2) Lactose | 35 mg |
| (3) Corn starch | 150 mg |
| (4) Microcrystalline cellulose | 30 mg |
| (5) Magnesium stearate | 5 mg |
| | Total 230 mg per tablet |

Components (1), (2) and (3), a two-thirds portion of component (4) and a half portion of component (5) are mixed and granulated. To these granules, the remaining portions of components (4) and (5) are added, and the whole mixture is tableted by compressive tableting.

EXAMPLE 17

| Capsules | |
|---|---|
| (1) Pivaloyloxymethyl 2-butyl-1-[[2'-(1H-tetrazol-5-yl)biphenyl-4-yl]methyl]-1H-benzimidazole-7-carboxylate | 10 mg |
| (2) Lactose | 90 mg |
| (3) Microcrystalline cellulose | 70 mg |
| (4) Magnesium stearate | 10 mg |
| | Total 180 mg per capsule |

Components (1), (2) and (3) and a half portion of component (4) are mixed and granulated. To these granules, the remaining portion of component (4) is added, and the whole mixture is packed in a gelatin capsule.

EXAMPLE 18

| Ophthalmic suspension | |
|---|---|
| (1) Compound 1 | 1.0 g |
| (2) Sodium dihydrogen phosphate | 0.2 g |
| (3) Sodium chloride | 0.9 g |
| (4) Polysorbate 80 | 0.1 g |
| (5) Benzalkonium chloride | 0.005 g |
| (6) Sodium edetate | 0.01 g |
| (7) 1 N sodium hydroxide | q.s. |
| (8) distilled water | Total 100 ml |

After components (2), (3), (4), (5) and (6) were dissolved in about 80 ml of component (8), component (7) was added to obtain pH 5.0. Component (8) was added to a total quantity of 100 ml, and the solution was filtered through a 0.2 μm membrane filter. Component (1), previously sterilized, was suspended in the solution to yield an ophthalmic suspension.

EXAMPLE 19

| Ophthalmic suspension | |
|---|---|
| (1) Compound 1 | 1.0 g |
| (2) Sodium acetate | 0.1 g |
| (3) hydroxypropylmethylcellulose | 0.2 g |
| (4) Sodium chloride | 0.9 g |
| (5) Methyl p-oxybenzoate | 0.026 g |
| (6) Propyl p-oxybenzoate | 0.014 g |
| (7) Sodium edetate | 0.01 g |
| (8) 1 N hydrochloric acid | q.s. |
| (9) distilled water | Total 100 ml |

Components (3), (5) and (6) are dissolved on heating under stirring in about 80 ml of component (9), and then the obtained solution is cooled to the room temperature. After components (2), (4) and (7) are dissolved in the solution, component (8) is added to obtain pH 5.0. Component (9) is added to a total quantity of 100 ml, and the solution is filtered through a 0.2 μm membrane filter. Component (1), previously sterilized, is suspended in the solution to yield an ophthalmic suspension.

EXAMPLE 20

| Ophthalmic suspension | |
|---|---|
| (1) Compound 1 | 2.0 g |
| (2) Carmellose sodium | 0.1 g |
| (3) Sodium chloride | 0.9 g |
| (4) Sodium acetate | 0.1 g |
| (5) Methyl p-oxybenzoate | 0.026 g |
| (6) Propyl p-oxybenzoate | 0.014 g |
| (7) 1 N hydrochloric acid | q.s. |
| (8) distilled water | Total 100 ml |

Components (5) and (6) are dissolved in about 80 ml of boiled component (8), and then the obtained solution are cooled to room temperature. After components (2), (3) and (4) are dissolved in the solution, component (7) is added to obtain pH 6.0. Component (8) is added to a total quantity of 100 ml, and the solution is filtered through a 0.2 μm membrane filter. Component (1), previously sterilized, is suspended in the solution to yield an ophthalmic suspension.

EXAMPLE 21

| Ophthalmic suspension | |
|---|---|
| (1) Compound 1 | 0.5 g |
| (2) Sodium acetate | 0.1 g |
| (3) Polyoxyethylene hydrogenated castor oil 60 | 0.1 g |
| (4) Glycerol | 2.6 g |
| (5) Benzalkonium chloride | 0.005 g |
| (6) Chlorobutanol | 0.3 g |
| (7) Sodium edetate | 0.01 g |
| (8) 1 N hydrochloric acid | q.s. |
| (9) distilled water | Total 100 ml |

Component (6) is dissolved on heating under stirring in about 80 ml of component (9), and then the obtained solution is cooled to the room temperature. After components (2), (3), (4), (5) and (7) are dissolved in the solution, component (8) is added to obtain pit 5.0. Component (9) is added to a total quantity of 100 ml, and the solution is filtered through a 0.2 μm membrane filter. Component (1), previously sterilized, is suspended in the solution to yield an ophthalmic suspension.

What is claimed is:

1. A method for treatment of glaucoma in a warm-blooded animal which comprises administering a pharmaceutically effective amount of (±)-1-(cyclohexyloxycarbonyloxy)ethyl 2-ethoxy-1-[[2'-(1H-tetrazol-5-yl)biphenyl-4-yl]methyl]-1H-benzimidazole-7-carboxylate or a pharmaceutically acceptable salt thereof, to an animal in need thereof.

2. A method of claim 1, which comprises local administration of the compound or salt thereof to the eye.

3. A method of claim 2, which comprises administration of the compound or salt thereof to the eye by eyedrops or ophthalmic ointment.

4. A method of claim 3, wherein the concentration of the compound or salt thereof in the ointment or eyedrop is 0.001 to 10 w/v % or w/w %.

5. A method of claim 4, wherein the compound or salt thereof is administered by eyedrops.

6. A method of claim 5, wherein the compound or salt thereof is administered in one to several drops about 3 to 6 times a day.

7. A method of claim 4, wherein the compound or salt thereof is administered by ophthalmic ointment.

8. A method of claim 7, wherein the compound or salt thereof is administered into the conjunctival sac.

9. A method of claim 8, wherein the compound or salt thereof is administered in amounts of about 0.1 to 0.2 g about 1 to 4 times a day.

10. A method for treatment of glaucoma caused by ocular hypertension in a warm-blooded animal which comprises administering a pharmaceutically effective amount of (±)-1-(cyclohexyloxycarbonyloxy)ethyl 2-ethoxy-1-[[2'-(1H-tetrazol-5-yl)biphenyl-4-yl]methyl]-1H-benzimidazole-7-carboxylate or a pharmaceutically acceptable salt thereof, to an animal in need thereof.

* * * * *